US00PP13824P29

(12) United States Plant Patent
Lamb et al.

(10) Patent No.: US PP13,824 P2
(45) Date of Patent: May 20, 2003

(54) SPATHIPHYLLUM PLANT NAMED 'EMERALD BEAUTY'

(75) Inventors: Ann Elizabeth Lamb, Sebring, FL (US); David R. Lilly, Boynton Beach, FL (US)

(73) Assignee: Twyford International Inc., Santa Paula, CA (US)

( * ) Notice: Subject to any disclaimer, the term of this patent is extended or adjusted under 35 U.S.C. 154(b) by 13 days.

(21) Appl. No.: 10/158,950

(22) Filed: May 31, 2002

(51) Int. Cl.[7] ..... A01H 5/00
(52) U.S. Cl. ..... Plt./364
(58) Field of Search ..... Plt./364

*Primary Examiner*—Bruce R. Campell
*Assistant Examiner*—Anne Marie Grünberg

(57) ABSTRACT

A distinct cultivar of Spathiphyllum plant named 'Emerald Beauty', characterized by its large, upright, somewhat outwardly arching and symmetrical plant habit; glossy and broad dark green leaves; rapid growth rate; white-colored spathes that are positioned just above the foliage on erect peduncles; and good postproduction longevity.

2 Drawing Sheets

BOTANICAL CLASSIFICATION/CULTIVAR DESIGNATION

Spathiphyllum hybrid cultivar Emerald Beauty.

BACKGROUND OF THE INVENTION

The present Invention relates to a new and distinct cultivar of Spathiphyllum plant, botanically known as Spathiphyllum hybrid, and hereinafter referred to by the cultivar name Emerald Beauty.

The new cultivar is a product of a planned and controlled breeding program conducted by the Inventors in Apopka, Fla. The objective of the breeding program is to create new Spathiphyllum cultivars with improved plant habit, dark green foliage and rapid plant growth rate.

The new cultivar originated from a cross-pollination made by the Inventors on Feb. 9, 1998 of the Spathiphyllum hybrid cultivar Sweet Pablo, disclosed in U.S. Plant Pat. No. 10,817, as the female or seed parent and the Spathiphyllum hybrid cultivar 31581, disclosed in U.S. Plant Pat. No. 10,893, as the male or pollen parent. Seeds resulting from the stated cross-pollination were harvested and sown on May 6, 1998. The cultivar Emerald Beauty was discovered and selected by the Inventors as a plant within the progeny of the stated cross-pollination in a controlled environment in Homestead, Fla., on Sep. 23, 1999.

Asexual propagation of the new cultivar by tissue culture since September, 1999, in a laboratory in Sebring, Fla., has shown that the unique features of this new Spathiphyllum plant are stable and reproduced true to type in successive generations of asexual propagation.

SUMMARY OF THE INVENTION

The new Spathiphyllum has not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Emerald Beauty'. These characteristics in combination distinguish 'Emerald Beauty' as a new and distinct Spathiphyllum cultivar:

1. Upright, somewhat outwardly arching and symmetrical plant habit; relatively large stature, suitable for 20-cm and larger containers.

2. Glossy and broad dark green leaves.

3. Rapid growth rate.

4. White-colored spathes that are positioned just above the foliage on erect peduncles.

5. Good postproduction longevity.

Plants of the new Spathiphyllum can be compared to plants of the female parent, the cultivar Sweet Pablo. In side-by-side comparisons conducted in Apopka, Fla., plants of the new Spathiphyllum differed from plants of the cultivar Sweet Pablo in the following characteristics:

1. Plants of the new Spathiphyllum were larger than plants of the cultivar Sweet Pablo.

2. Leaves of plants of the new Spathiphyllum were darker green in color, more broad, and thicker than leaves of plants of the cultivar Sweet Pablo.

3. Spathes of plants of the new Spathiphyllum were ovate to elliptic in shape whereas spathes of plants of the cultivar Sweet Pablo were narrower and lanceolate in shape.

Plants of the new Spathiphyllum can be compared to plants of the male parent, the cultivar 31581. In side-by-side comparisons conducted in Apopka, Fla., plants of the new Spathiphyllum differed from plants of the cultivar 31581 in the following characteristics:

1. Plants of the new Spathiphyllum were considerably larger and taller than plants of the cultivar 31581.

2. Leaves of plants of the new Spathiphyllum were lighter green in color, larger and more broad than leaves of plants of the cultivar 31581.

Plants of the new Spathiphyllum are most similar to plants of the Spathiphyllum cultivar Linda, not patented. However, in side-by-side comparisons conducted in Apopka, Fla., plants of the new Spathiphyllum differed from plants of the cultivar Linda in the following characteristics:

1. Plants of the new Spathiphyllum grew more rapidly than plants of the cultivar Linda.

2. Leaves of plants of the new Spathiphyllum were darker green in color and glossier than leaves of plants of the cultivar Linda.

3. Leaves of plants of the new Spathiphyllum were broader, thicker and more rugose than leaves of plants of the cultivar Linda.

4. Spathes of plants of the new Spathiphyllum were held just above the foliage whereas spathes of plants of the cultivar Linda were held well above the foliage.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Spathiphyllum.

The photograph on the first sheet comprises a side perspective view of typical plants of 'Emerald Beauty' grown in a 35-cm container.

The photograph on the second sheet comprises a close-up view of typical inflorescences of 'Emerald Beauty'.

DETAILED BOTANICAL DESCRIPTION

The aforementioned photographs and following observations and measurements describe 15-month old plants (from planting rooted tissue-cultured plantlets) grown during the winter in Homestead, Fla., in a polypropylene-covered shadehouse and under commercial production conditions in 35-cm containers with three plantlets per container. During the production of the plants, day temperatures ranged from 70 to 90° F., night temperatures ranged from 65 to 75° F., and light levels were about 1,500 to 2,000 foot-candles.

In the following description, color references are made to The Royal Horticultural Society Colour Chart, 1995 Edition, except where general terms of ordinary dictionary significance are used.

Botanical classification: Spathiphyllum hybrid cultivar Emerald Beauty.

Parentage:

*Female parent.*—Spathiphyllum hybrid cultivar Sweet Pablo, disclosed in U.S. Plant Pat. No. 10,817.

*Male parent.*—Spathiphyllum hybrid cultivar 31581, disclosed in U.S. Plant Pat. No. 10,893.

Propagation:

*Type.*—By tissue culture.

*Time to initiate roots on a tissue-cultured cutting.*—Summer: About 6 to 8 days at 70 to 90° F. day temperature and 65 to 75° F. night temperature. Winter: About 7 to 10 days at 70 to 90° F. day temperature and 65 to 75° F. night temperature.

*Time to produce a fully-rooted tissue-cultured plantlet.*—Summer: About 70 days at 70 to 90° F. day temperature and 65 to 75° F. night temperature. Winter: About 84 days at 70 to 90° F. day temperature and 65 to 75° F. night temperature.

*Root description.*—Primary roots, thick, fleshy; lateral branch roots, fine; primary and lateral roots white in color.

*Rooting habit.*—Freely branching.

Plant description:

*Plant shape.*—Upright, somewhat outwardly arching and symmetrical plant habit; relatively large stature.

*Growth habit.*—Erect when young, becoming somewhat outwardly arching as leaves develop. Freely clumping and full appearance; about 12 clumps per plant. Plants of the new Spathiphyllum are typically grown in 20-cm and larger containers.

*Plant height.*—About 80 to 85 cm from soil level to top of leaf plane and about 85 to 97 cm from soil level to spathe apices.

*Plant spread.*—About 105 to 116 cm.

*Growth rate.*—Rapid growth rate; from tissue-cultured plantlets, about 10 months are required to produce finished flowering plants in 20-cm containers and about 12 months are required to produced finished flowering plants in 35-cm containers.

*Foliage description.*—Length: About 35 to 43 cm. Width: About 17 to 22 cm. Shape: Broadly elliptic to ovate. Apex: Acuminate. Base: Cuneate to obtuse. Margin: Entire; moderately undulate. Aspect: Initially upright, then perpendicular to the petiole and outwardly arching; leaves curved downward towards the apex. Surface: Midrib sunken on upper surface and prominent on lower surface; upper surface of blade convex between veins, rugose. Texture, upper and lower surfaces: Leathery, smooth, glabrous, durable and flexible. Venation pattern: Pinnate; about 20 pairs of primary veins per leaf. Color: Young and fully expanded leaves, upper surface: 139A; glossy. Young and fully expanded leaves, lower surface: 137B to 137C; dull. Midrib, upper surface: 137A. Midrib, lower surface: 146D. Petiole: Length: About 40 to 45 cm. Diameter, just below the geniculum: About 6 cm. Petiole sheath, length: About 30 to 35 cm. Petiole sheath, diameter at midpoint: About 1.2 cm. Petiole sheath, apex: Flush with the petiole. Geniculum length: About 6 cm. Geniculum diameter: About 8 mm. Geniculum aspect: Straight to curved. Color: Petiole: 137A. Petiole sheath: 137A to 137B. Geniculum: 137B tinged with 146B.

Inflorescence description:

*Inflorescence arrangement/quantity.*—Concave spathes with spadices held just above the foliage on erect peduncles. Freely flowering; typically about five developing and open spathes per plant at one time; inflorescences arise from the petiole sheath.

*Time to flower.*—Inflorescences are initiated in the winter and early spring in Homestead, Fla.

*Inflorescence longevity.*—Spathes generally maintain white color for about four weeks on the plant becoming entirely green after about six weeks. As cut flowers, spathes maintain good substance for about seven days.

*Fragrance.*—Moderately fragrant, sweet, typical of Spathiphyllum; most noticeable in the morning.

*Inflorescence buds.*—Length: About 13 cm. Diameter, widest point: About 1.2 cm. Shape: Spindle-shaped. Color: 155A; venation, 145A; towards the apex, 146D.

*Spathe.*—Length: About 23 to 27 cm. Width: About 10 to 13 cm. Depth: About 4 cm. Shape: Elliptic to ovate. Apex: Acuminate; twisted. Base: Cuneate to obtuse. Aspect: Concave, curling over the spadix. Color Front surface: 155D; midrib, 155D tinged with 191D; apex, 155D. Back surface: 155D; midrib, 144A streaked with 137B; apex, 155D tinged with 146D. Front surface with subsequent development: 146B; midrib, 137B; apex, 137A to 137B. Back surface with subsequent development: 146B to 146C; midrib, 137A to 137B; apex, 137A.

*Spadix.*—Length: About 11 cm. Diameter: About 1.8 cm. Color: 158A gradually becoming closer to 137A with development. Quantity of flowers per spadix: About 450. Stamens: Anthers and filaments are minute and not clearly visible. Pollen: Abundant. Pollen color: 158D, becoming closer to 158A with subsequent development. Pistils: Conical; pistillate flowers extend about 3 mm beyond the staminate flowers; 158A in color.

*Peduncle.*—Length: About 70 to 76 cm. Diameter, at midpoint: About 8 mm. Aspect: Straight, erect. Color: 137A.

*Fruit.*—Type: Berry. Length: About 1 cm. Diameter: About 7 mm. Shape: Elliptic. Color: Darker than, but closest to 137A; when ripe, tinged with 19C.

*Seed.*—Quantity per fruit: About one to six. Quantity per inflorescence: About 700 or more. Length: About 3 mm. Shape: Reniform. Texture: Slightly pitted. Color: Light brown.

Disease/pest resistance: Plants of the new Spathiphyllum have not been observed to be resistant to pathogens or pests common to Spathiphyllum.

Temperature tolerance: Plants of the new Spathiphyllum have been observed to tolerate temperatures from 45 to 104° F.

It is claimed:

1. A new and distinct cultivar of Spathiphyllum plant named ‘Emerald Beauty’, as illustrated and described.

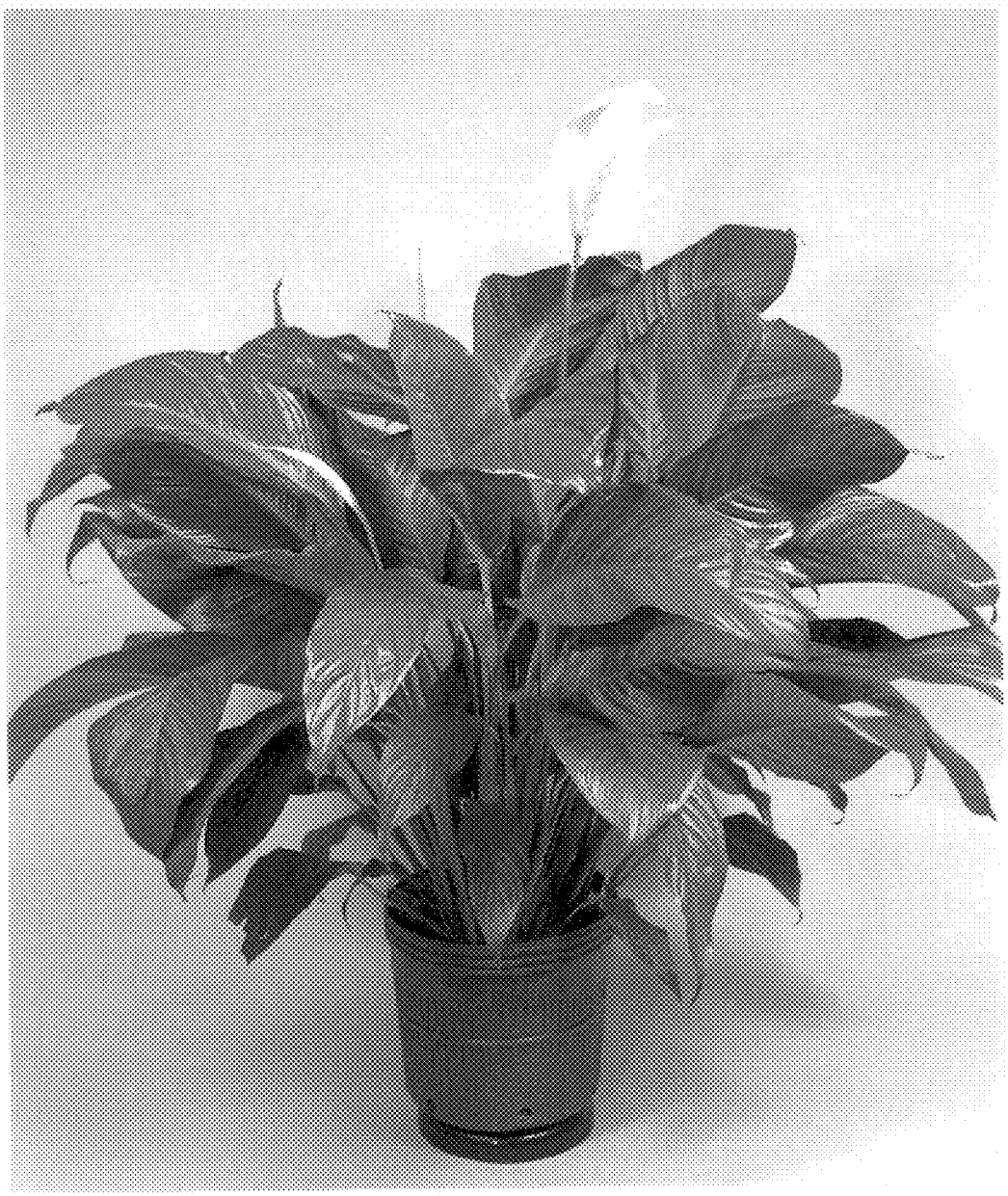

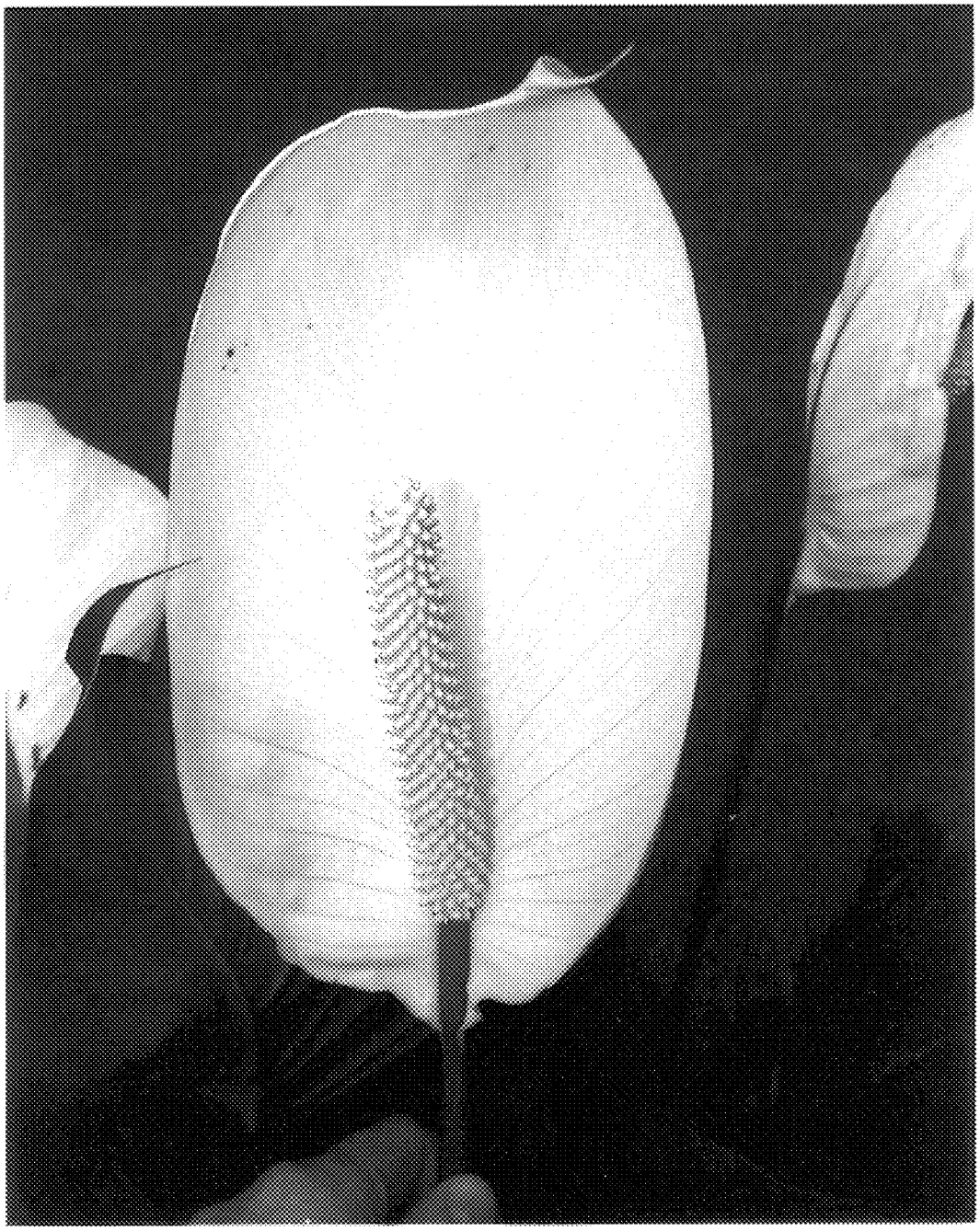

* * * * *